US009796643B2

(12) United States Patent
Buchanan et al.

(10) Patent No.: US 9,796,643 B2
(45) Date of Patent: Oct. 24, 2017

(54) HYDROCARBON DEHYDROCYCLIZATION IN THE PRESENCE OF CARBON DIOXIDE

(71) Applicant: ExxonMobil Chemical Patents Inc., Baytown, TX (US)

(72) Inventors: John S. Buchanan, Flemington, NJ (US); Paul F. Keusenkothen, Houston, TX (US); David W. Maher, Spring, TX (US); Jaime A. Valencia, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/240,624

(22) Filed: Aug. 18, 2016

(65) Prior Publication Data
US 2017/0088486 A1 Mar. 30, 2017

Related U.S. Application Data

(60) Provisional application No. 62/232,609, filed on Sep. 25, 2015, provisional application No. 62/298,655, filed on Feb. 23, 2016.

(30) Foreign Application Priority Data

Nov. 19, 2015 (EP) ..................................... 15195311
Apr. 29, 2016 (EP) ..................................... 16167672

(51) Int. Cl.
| | | |
|---|---|---|
| *C07C 2/76* | (2006.01) |
| *C07C 1/12* | (2006.01) |
| *B01J 29/06* | (2006.01) |
| *B01J 23/755* | (2006.01) |
| *B01J 23/46* | (2006.01) |
| *B01J 23/652* | (2006.01) |
| *B01J 23/58* | (2006.01) |
| *B01J 29/70* | (2006.01) |
| *B01J 29/78* | (2006.01) |
| *B01J 37/08* | (2006.01) |
| *B01J 29/69* | (2006.01) |
| *B01J 23/656* | (2006.01) |
| *B01J 23/63* | (2006.01) |
| *B01J 23/86* | (2006.01) |
| *B01J 23/78* | (2006.01) |
| *B01J 23/889* | (2006.01) |
| *B01J 23/83* | (2006.01) |
| *B01J 29/40* | (2006.01) |
| *B01J 29/48* | (2006.01) |
| *B01J 29/65* | (2006.01) |
| *B01J 37/16* | (2006.01) |
| *B01J 8/02* | (2006.01) |

(52) U.S. Cl.
CPC ............... *C07C 2/76* (2013.01); *B01J 8/0278* (2013.01); *B01J 23/462* (2013.01); *B01J 23/58* (2013.01); *B01J 23/63* (2013.01); *B01J 23/6522* (2013.01); *B01J 23/6562* (2013.01); *B01J 23/755* (2013.01); *B01J 23/78* (2013.01); *B01J 23/83* (2013.01); *B01J 23/866* (2013.01); *B01J 23/8892* (2013.01); *B01J 29/06* (2013.01); *B01J 29/405* (2013.01); *B01J 29/48* (2013.01); *B01J 29/655* (2013.01); *B01J 29/69* (2013.01); *B01J 29/708* (2013.01); *B01J 29/7084* (2013.01); *B01J 29/7088* (2013.01); *B01J 29/7092* (2013.01); *B01J 29/7096* (2013.01); *B01J 29/7861* (2013.01); *B01J 29/7869* (2013.01); *B01J 29/7876* (2013.01); *B01J 29/7884* (2013.01); *B01J 29/7892* (2013.01); *B01J 37/08* (2013.01); *B01J 37/16* (2013.01); *C07C 1/12* (2013.01); *B01J 2208/02* (2013.01); *B01J 2229/18* (2013.01); *C07C 2529/06* (2013.01)

(58) Field of Classification Search
CPC ......... C07C 2/76; C07C 1/12; C07C 2529/06; B01J 29/06; B01J 23/755; B01J 23/462; B01J 23/6522; B01J 23/58; B01J 23/63; B01J 23/8892; B01J 23/83; B01J 29/405; B01J 29/48; B01J 29/655; B01J 29/708; B01J 37/08; B01J 2208/02
See application file for complete search history.

(56) References Cited

U.S. PATENT DOCUMENTS

| | | |
|---|---|---|
| 3,960,978 A | 6/1976 | Givens et al. |
| 4,021,502 A | 5/1977 | Plank et al. |
| 4,150,062 A | 4/1979 | Garwood et al. |
| 4,227,992 A | 10/1980 | Garwood et al. |
| 4,439,409 A | 3/1984 | Puppe et al. |
| 4,456,781 A | 6/1984 | Marsh et al. |

(Continued)

FOREIGN PATENT DOCUMENTS

| | | |
|---|---|---|
| EP | 293032 | 11/1988 |
| EP | 2862849 | 4/2015 |

(Continued)

OTHER PUBLICATIONS

Yamauchi et al., Sekiyu Gakkaishi, 37, (3), 278-284 (1994).

(Continued)

*Primary Examiner* — Jafar Parsa

(57) ABSTRACT

The invention relates to converting non-aromatic hydrocarbon in the presence of $CO_2$ to produce aromatic hydrocarbon. $CO_2$ methanation using molecular hydrogen produced during the aromatization increases aromatic hydrocarbon yield. The invention also relates to equipment and materials useful in such upgrading, to processes for carrying out such upgrading, and to the use of such processes for, e.g., natural gas upgrading.

10 Claims, No Drawings

(56) References Cited

U.S. PATENT DOCUMENTS

| | | | |
|---|---|---|---|
| 4,826,667 | A | 5/1989 | Zones et al. |
| 4,954,325 | A | 9/1990 | Rubin et al. |
| 5,026,937 | A | 6/1991 | Bricker |
| 5,236,575 | A | 8/1993 | Bennett et al. |
| 5,250,277 | A | 10/1993 | Kresge et al. |
| 5,362,697 | A | 11/1994 | Fung et al. |
| 5,633,417 | A | 5/1997 | Beck et al. |
| 5,675,047 | A | 10/1997 | Beck et al. |
| 6,077,498 | A | 6/2000 | Diaz Cabanas et al. |
| 8,692,043 | B2 | 4/2014 | Lauritzen et al. |
| 8,835,706 | B2 | 9/2014 | Iyer et al. |
| 2009/0209794 | A1 | 8/2009 | Lauritzen et al. |

FOREIGN PATENT DOCUMENTS

| | | |
|---|---|---|
| WO | 97/17290 | 5/1997 |
| WO | 2006/068814 | 6/2006 |
| WO | 2008/002343 | 1/2008 |
| WO | 2009/124960 | 10/2009 |
| WO | 2010140005 | 12/2010 |

OTHER PUBLICATIONS

Smith et al., International Journal of Chemical Reactor Engineering, b. 8 Review R4 (2010), "A Review of the Water Gas Shift Reaction Kinetics".

Chetina et al., Applied Catalysis A: General 131 (1995) 7-14, "Aromatization of ethane over Pt,GaHZSM-5 catalyst and the effect of intermetallic hydrogen acceptor on the reaction".

Hattori et al., Chemistry Letters, pp. 629-630, (1992), "Catalytic Reduction of Carbon Dioxide on Zn-loaded HZSM-5 Accompanying Aromatization of Propane".

Kitagawa et al., Journal of Catalysis 101, 12-18 (1986), "Transformation of Propane into Aromatic Hydrocarbons over ZSM-5 Zeolites".

Roessner et al., Studies in Surface Science and Catalysis 130, Dec. 2000, pp. 2519-2524, "Aromatization of Ethane on Modified Zeolites in the Presence of Co-Reactants".

Tingey, G.L., Journal of Physical Chemistry, vol. 70, No. 5, May (1966), "Kinetics of the Water-Gas Equilibrium Reaction. I. The Reaction of Carbon Dioxide with Hydrogen".

Toth et al., Journal of Catalysis 330 (2015) 1-5, "Reactions of ethane with $CO_2$ over supported Au".

Yaccato et al., Applied Catalysis A: General 296 (2005) 30-48, "Competitive CO and CO2 Methanation Over Supported Noble Metal Catalyst in High Throughput Scanning Mass Spectrometer".

Dong Q. et al, "Studies on Mo/HZSM-5 complex catalyst for methane aromatization", Jounal of Natural Gas Chemistry, vol. 13, Jan. 1, 2004, pp. 36-40.

Ohnishi R. et al., "Catalytic Dehydrocondensation of Methane with CO and CO2 toward Benzene and Napthalene on Mo/HZSM-5 and Fe/Co-Modified Mo/HZSM-5", Journal of Catalysis, Academic Press, vol. 182, No. 1, Feb. 15, 1999, pp. 92-103.

Weckhuysen B.M. et al., "Conversion of Methane to Benzene over Transition Metal Ion ZSM-5 Zeolites—1. Catalytic Characterization", Journal of Catalysis, Academic Press, vol. 175, No. 2, Apr. 25, 1998, pp. 338-346.

Li et al., "$CO_2$ atmosphere-enhanced methanol aromatization over the NiO-HZSM-5 catalyst", The Royal Society of Chemistry, RSC Advances, vol. 4, pp. 44377-44385, 2014.

HYDROCARBON DEHYDROCYCLIZATION IN THE PRESENCE OF CARBON DIOXIDE

CROSS-REFERENCE TO RELATED APPLICATIONS

This invention claims priority to and the benefit of U.S. Patent Application Ser. Nos. 62/232,609 filed Sep. 25, 2015 and 62/298,655 filed Feb. 23, 2016; and European Patent Application Nos. 15195311.4 filed Nov. 19, 2015, and 16167672.1 filed Apr. 29, 2016, all of which are herein incorporated by reference in their entireties. The following related cases are also incorporated by reference in their entireties: U.S. Patent Application Ser. No. 62/234,262, European Patent Application No. 15195314.8, U.S. Patent Application Ser. No. 62/234,240, European Patent Application No. 15197698.2, U.S. Patent Application Ser. No. 62/247,795, European Patent Application No. 15197700.6, U.S. Patent Application Ser. No. 62/248,374, European Patent Application No. 15197702.2, U.S. Patent Application Ser. No. 62/253,268, U.S. Patent Application Ser. No. 62/326,918, European Patent Application No. 16175163.1, U.S. Patent Application Ser. No. 62/299,730, European Patent Application No. 16167395.9, U.S. Patent Application Ser. No. 62/313,288, European Patent Application No. 16173587.3, U.S. Patent Application Ser. No. 62/313,306 and European Patent Application No. 16173980.0.

FIELD

The invention relates to converting non-aromatic hydrocarbon in the presence of $CO_2$ to produce aromatic hydrocarbon. The invention also relates to equipment and materials useful in such upgrading, to processes for carrying out such upgrading, and to the use of such processes for, e.g., natural gas upgrading.

BACKGROUND

Aromatic hydrocarbon compounds such as benzene, toluene, and xylenes ("BTX") are frequently used for producing transportation fuels and petrochemicals such as styrene, phenol, nylon, polyurethanes, and many others. Processes have been developed for producing aromatic hydrocarbon from relatively inexpensive feeds, e.g., from paraffinic $C_4$-feeds. The processes typically are carried out using a catalyst comprising molecular sieve, such as ZSM-5 and at least one dehydrogenation metal. Aromatic hydrocarbon can be recovered from unreacted feed and reaction byproducts in an aromatics recovery system located downstream of the aromatization process. Yield of aromatic hydrocarbon has been found to be limited by the presence of molecular hydrogen produced during hydrocarbon dehydrogenation. Aromatic hydrocarbon yield has also been found to be limited by side reactions such as hydrogenolysis and coking. Hydrogenolysis undesirably produces a light saturated hydrocarbon byproduct. Coking produces undesirable catalyst deposits, which decrease catalyst activity and increase reactor pressure drop.

Light hydrocarbon is often available in combination with $CO_2$, and these resources have generated considerable interest as potential feeds to aromatization processes. Although $CO_2$ can be separated from the feed upstream of the aromatization, this approach is typically undesirable in view of the inefficiency and complexity of the refrigeration equipment used to do so. $CO_2$ can also be separated downstream of the aromatization, but doing so can bottleneck the aromatic hydrocarbon recovery system. These difficulties can be at least partially overcome by converting $CO_2$ to CO and water during the aromatization. As reported in Yamaouchi et al, Sekiyu Gakkaishi, 37, (3), 278-284 (1994), aromatization of a feed comprising propane and $CO_2$ can be carried out using a catalyst comprising ZSM-5 loaded with Zn, Ga, or Pt. The reference reported an increase in aromatic hydrocarbon yield at a reaction temperature of about 823° K, which was attributed to the beneficial effects of a reverse water gas shift reaction ("RWGS"): $CO_2+H_2 \rightarrow CO+H_2O$. Particularly with Pt-ZSM-5 catalysts, the reference reported an improvement in the yield of aromatic hydrocarbon resulting from molecular hydrogen conversion in the reverse water gas shift reaction. The reference also reports an undesirable hydrogenolysis increase during simultaneous aromatization and RWGS, which can bottleneck the aromatics recovery system. Increased methane production from hydrogenolysis has also been found to increase hydrocarbon partial pressure during the aromatization, leading to an increase in the rate of catalyst coking. Although the amount of hydrogenolysis can be mitigated (e.g., by adding an attenuating metal to the catalyst as disclosed in U.S. Pat. No. 8,692,043), this significantly increases catalyst complexity.

It is also observed that light hydrocarbon aromatization and RWGS are endothermic reactions. Combining these two reactions for light hydrocarbon aromatization in the presence of $CO_2$ for increased aromatic hydrocarbon yield may also increase reactor complexity and decrease the process's energy efficiency. For example, the aromatization reactor vessel may need modification so that additional heat can be added to support the RWGS reaction. The additional heat can be produced by combustion of a fuel, but at an increased energy debit over the energy needed for the aromatization reaction.

There is therefore a need for improved processes and catalysts for aromatization of substantially non-aromatic hydrocarbon in the presence of $CO_2$.

SUMMARY

The invention is based in part on the development of processes for aromatizing substantially non-aromatic hydrocarbon in the presence of $CO_2$ by catalytically converting at least part of the $CO_2$ to methane and water ("$CO_2$ methanation"): $CO_2+4H_2 \rightarrow CH_4+2H_2O$. The increased molecular hydrogen consumption during $CO_2$ methanation (four times more than RWGS on a molar basis) leads to an improved yield of aromatic hydrocarbon. Moreover, the exothermic $CO_2$ methanation reaction can provide heat to the endothermic aromatization reaction, resulting in a more efficient process than aromatization in combination with RWGS. Contrary to expectations, the increase in hydrocarbon partial pressure during aromatization resulting from $CO_2$ methanation does not significantly increase the rate of catalyst coking.

Accordingly, certain aspects of the invention relate to a hydrocarbon conversion process which utilizes a feed comprising ≥1 wt. % of $C_{2+}$ non-aromatic hydrocarbon and ≥0.1 wt. % of $CO_2$. The process includes contacting the feed with first and second catalysts. The first catalyst includes (i) ≥0.005 wt. % of a dehydrogenation component which comprises one or more of Ga, Zn, Mo, W, La, Pt, and Pd, and (ii) ≥10 wt. % of a molecular sieve component which comprises at least one molecular sieve having a Constraint Index in the range of from 1 to 12. The second catalyst includes ≥0.005 wt. % of a $CO_2$ conversion component, with the $CO_2$ conversion component comprising one or more of Ru, Rh, Ni, Co, and Fe. The process includes exposing the feed to the first catalyst under conversion conditions effective for (i) converting ≥10 wt. % of the feed's $C_{2+}$ non-aromatic hydrocarbon to aromatic hydrocarbon and molecular hydrogen and (ii) increasing aromatic hydrocarbon yield by reacting ≥1 wt. % of the feed's $CO_2$ with at least a portion of the molecular hydrogen in the presence of the second catalyst to produce methane and water.

Other aspects of the invention relate to an active material for hydrocarbon aromatization in the presence of $CO_2$. The active material includes ≥10 wt. % a first catalyst and ≥10 wt. % of a second catalyst. The first catalyst comprises ≥0.005 wt. % of a dehydrogenation component which includes one or more of Ga, Zn, Mo, W, La, Pt, and Pd. The first catalyst further comprises ≥10 wt. % of a molecular sieve component which comprises at least one molecular sieve having a Constraint Index in the range of from 1 to 12. The second catalyst comprises ≥0.005 wt. % of a $CO_2$ conversion component which includes one or more of Ru, Rh, Ni, Co, and Fe. In certain aspects, the active material is in the form of a mixture of particles, with a first portion of the mixture's particles comprising the first catalyst and a second portion of the mixture's particles comprising the second catalyst. Alternatively or in addition, the active material can be in the form of a composite which comprises the first and second catalysts and/or in the form of a bed of the first catalyst located upstream of a bed of the second catalyst.

In still other aspects, the invention relates to a process for making an active material for hydrocarbon aromatization in the presence of $CO_2$. The process includes contacting a molecular sieve and a dehydrogenation precursor which includes a dehydrogenation component. The molecular sieve has a Constraint Index in the range of from 1 to 12. The dehydrogenation component comprises one or more of Ga, Zn, Mo, W, La, Pt, and Pd. The contacting is carried out under conditions effective for transferring to the molecular sieve at least a portion of the first precursor's dehydrogenation component to produce a loaded molecular sieve. The loaded molecular sieve comprises ≥0.005 wt. % of one or more of transferred Ga, Zn, Mo, W, La, Pt, and Pd. The process also includes contacting an oxide matrix with a second precursor which includes a $CO_2$ conversion component. The oxide matrix includes one or more of oxide of chromium, oxide of aluminum, oxide of magnesium, oxide of manganese, oxide of cerium, oxide of zirconium, oxide of titanium, and oxide of thorium. The $CO_2$ conversion component includes one or more of Ru, Rh, Ni, Co, and Fe. The contacting is carried out under conditions effective for transferring to the matrix at least a portion of the $CO_2$ conversion component to produce a loaded matrix comprising ≥0.005 wt. % of one or more of transferred Ru, Rh, Ni, Co, and Fe. The process includes calcining the loaded molecular sieve and the loaded matrix, and reducing the calcined loaded molecular sieve and the calcined loaded matrix to produce the active material.

In other aspects, a matrix is not used, and the active material is produced by contacting the molecular sieve with the first and second precursors (simultaneously, or one before the other) in order to produce a loaded molecular sieve comprising ≥0.005 wt. % of one or more of Ga, Zn, Mo, W, La, Pt, and Pd transferred from the first precursor and ≥0.005 wt. % of one or more of transferred Ru, Rh, Ni, Co, and Fe transferred from the second precursor. The loaded molecular sieve can be calcined and reduced to produce the active material.

In other aspects, the invention relates to an apparatus for carrying out the process.

DETAILED DESCRIPTION

Certain aspects of the invention relate to a process for upgrading a feed comprising $CO_2$ and non-aromatic hydrocarbon. These aspects include contacting the feed with catalytically effective amounts of the specified first and second catalysts under conversion conditions that are effective for converting the feed's non-aromatic hydrocarbon to aromatic hydrocarbon and molecular hydrogen. The first catalyst, which includes dehydrocyclization functionality, comprises (i) ≥0.005 wt. % of a dehydrogenation component which includes one or more of Ga, Zn, Mo, W, La, Pt, and Pd; and (ii) ≥10 wt. % of a molecular sieve component, which includes at least one molecular sieve having a Constraint Index in the range of from 1 to 12. The second catalyst comprises ≥0.005 wt. % of a $CO_2$ conversion component, e.g., ≥0.005 wt. % of a $CO_2$ methanation component, such as ≥0.005 wt. % of one or more of Ru, Rh, Ni, Co, and Fe. Aromatic hydrocarbon yield is increased by catalytically converting feed $CO_2$ with at least a portion of the molecular hydrogen produced in the dehydrocyclization to produce methane and water ($CO_2$ methanation). Methane and water produced during the $CO_2$ methanation reaction are readily separated from the aromatic hydrocarbon product, e.g., by condensing the aromatic hydrocarbon and water into the liquid phase. One or more vapor liquid separators (e.g., knock out drums) can be used for separating gaseous methane from the condensed liquid. Gravity separation (e.g., one or more settling tanks) can be used for separating water from the desired aromatic hydrocarbon product.

The observed increase in aromatic hydrocarbon yield is surprising. Even though the $CO_2$ methanation consumes more molecular hydrogen on a molar basis than do conventional processes such as RWGS, $CO_2$ methanation also produces one mole of hydrocarbon ($CH_4$) for each mole of $CO_2$ consumed. It was believed that the additional hydrocarbon would lead to excessive hydrocarbon partial pressure, which in turn would lead to rapid catalyst deactivation as a result of increased coke-make. This has been found to not be the case, particularly when utilizing the specified dehydrocyclization and $CO_2$ conversion catalysts. It has also been found that this effect can be enhanced to provide a further decrease in the rate of dehydrocyclization catalyst deactivation, when (i) less then all of the feed's $CO_2$ is consumed during the $CO_2$ methanation and/or (ii) less than all of the molecular hydrogen produced during the dehydrocyclization is consumed during the $CO_2$ methanation. While not wishing to be bound by any theory or model, it is believed that the enhancements result at least in part from (i) catalyst coke conversion by the reaction $CO_2 + C \rightarrow 2CO$, when $CO_2$ methanation consumes less than all of the feed's $CO_2$, and (ii) catalyst coke methanation, when $CO_2$ methanation consumes less than all of the molecular hydrogen produced during the dehydrocyclization.

The exothermic nature of the $CO_2$ methanation reaction can be used advantageously to make reactors for carrying out the process more efficient by making them more isothermal. Particularly when the process is carried out with one or more catalyst beds containing a mixture of dehydrocyclization catalyst and $CO_2$ conversion catalyst and/or when using a composited catalyst which includes a catalyst component active for dehydrocyclization and a catalyst component active for $CO_2$ conversion. Heat released by the exothermic $CO_2$ methanation reaction is available for efficient transfer to the endothermic dehydrocyclization reaction, e.g., via reactor components, including via the catalyst bed or composite. Complex means for heating the dehydrocyclization catalyst beds are thus avoided, such as those needed when endothermic RWGS is used with endothermic dehydrocyclization. The $CO_2$ methanation reaction is compatible with RWGS, and the reactions can be combined if desired, e.g., when there is a need for the CO produced by RWGS.

Certain aspects of the invention, including those which relate to producing aromatic hydrocarbon from a feed comprising $CO_2$ and non-aromatic hydrocarbon, will now be described in more detail. The invention is not limited to these aspects, and this description is not meant to foreclose other aspects within the broader scope of the invention. In this description and appended claims, reference will be made to the following defined terms.

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule. The term "$C_{n-}$" hydrocarbon means hydrocarbon having no more than n carbon atom(s) per molecule. The term "hydrocarbon" means a class of compounds containing hydrogen bound to carbon, and encompasses (i) saturated hydrocarbon, (ii) unsaturated hydrocarbon, and (iii) mixtures of hydrocarbons, and including mixtures of hydrocarbon compounds (saturated and/or unsaturated), such as mixtures of hydrocarbon compounds having different values of n.

The terms "alkane" and "paraffinic hydrocarbon" mean substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes. Aliphatic hydrocarbon means hydrocarbon that is substantially free of hydrocarbon compounds having carbon atoms arranged in one or more rings.

The term "unsaturate" and "unsaturated hydrocarbon" refer to one or more $C_{2+}$ hydrocarbon compounds which contain at least one carbon atom directly bound to another carbon atom by a double or triple bond. The term "olefin" refers to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. The term "aromatics" and "aromatic hydrocarbon" mean hydrocarbon compounds containing at least one aromatic ring. Non-aromatic hydrocarbon is hydrocarbon comprising ≤1 wt. % of carbon atoms included in aromatic rings.

The term "Periodic Table" means the Periodic Chart of the Elements, as it appears on the inside cover of The Merck Index, Twelfth Edition, Merck & Co., Inc., 1996.

The term "reaction zone" or "reactor zone" mean a location within a reactor, e.g., a specific volume within a reactor, for carrying out a specified reaction. A reactor or reaction stage can encompass one or more reaction zones. More than one reaction can be carried out in a reactor, reactor stage, or reaction zone. For example, a reaction stage can include a first zone for carrying out first and second reactions and a second zone for carrying out a third reaction, where the first reaction (e.g., dehydrocyclization) can be the same as or different from the second reaction, and the third reaction (e.g., $CO_2$ methanation) can be the same as or different from the second reaction.

"Dehydrocyclization" means removing hydrogen from and cyclizing a non-cyclic hydrocarbon to produce aromatic hydrocarbon and typically (i) cyclo-paraffin and/or (ii) cyclo-olefin. Dehydrocyclization can be carried out in one step which includes both dehydrogenation and cyclization. Dehydrocyclization can be carried out in one step, in two steps, e.g., dehydrogenation followed by cyclization of the dehydrogenated intermediate; or in three or more steps, e.g., normal paraffin dehydrogenation, cyclization of the olefinic intermediate, and additional dehydrogenation (aromatization) of the cyclo-olefin intermediate. The dehydrocyclization (including any dehydrogenation carried out in connection with dehydrocyclization) is "non-oxidative" meaning that the reaction is carried out with little if any oxidative coupling of feed hydrocarbon, intermediate hydrocarbon (if any), or dehydrocyclization product.

The term "selectivity" refers to the production (on a weight basis) of a specified compound in a catalytic reaction. As an example, the phrase "a light hydrocarbon conversion reaction has a 100% selectivity for aromatic hydrocarbon" means that 100% of the light hydrocarbon (weight basis) that is converted in the reaction is converted to aromatic hydrocarbon. When used in connection with a specified reactant, the term "conversion" means the amount of the reactant (weight basis) consumed in the reaction. For example, when the specified reactant is $C_4$ paraffinic hydrocarbon, 100% conversion means 100% of the $C_4$ paraffinic hydrocarbon is consumed in the reaction. Yield (weight basis) is conversion times selectivity.

The invention includes reacting a feed comprising $CO_2$ and non-aromatic hydrocarbon to (i) selectively convert at least a portion of the feed's non-aromatic hydrocarbon to aromatic hydrocarbon and molecular hydrogen and (ii) increase the yield of aromatic hydrocarbon by reacting at least a portion of the feed's $CO_2$ with at least a portion of the molecular hydrogen to form methane and water. The dehydrocyclization of the feed's $C_{2+}$ non-aromatic hydrocarbon and the methanation of the feed's $CO_2$ can be effectively carried out by exposing the feed to the specified first and second catalysts under conditions which include a temperature in range of from 400° C. to 700° C., a pressure ≥10 psia (68.9 kPa), and a weight hourly space velocity ("WHSV"). WHSV is based on (i) the weight of the $C_{2+}$ hydrocarbon and (ii) the combined weight of the first and second catalyst) in the range of 0.1 $hr^{-1}$ to 20 $hr^{-1}$. It has been found that when these conditions are used with the specified $CO_2$ conversion catalyst, the $CO_2$ conversion has a greater selectivity for methane than CO, e.g., ≥10% greater selectivity for methane, such as ≥25% greater selectivity. Representative feeds will now be described in more detail. The invention is not limited to these feeds, and this description is not meant to foreclose other feeds within the broader scope of the invention.

Representative Feeds

The feed typically comprises ≥1 wt. % of $C_{2+}$ non-aromatic hydrocarbon and ≥0.1 wt. % of $CO_2$, e.g., ≥10 wt. % of $C_{2+}$ non-aromatic hydrocarbon and ≥1 wt. % of $CO_2$, such as ≥5 wt. % $CO_2$. The non-aromatic hydrocarbon is generally one or more $C_2$ to $C_9$ non-aromatic hydrocarbon compounds, e.g., one or more light hydrocarbon (i.e., $C_2$ to $C_5$) compounds, such as one or more paraffinic light hydrocarbon compounds. For example, the feed can comprise $CO_2$ and ≥1 wt. % based on the weight of the feed of one or more of (i) paraffinic $C_2$ to $C_9$ hydrocarbon, (ii) aliphatic $C_2$ to $C_9$ hydrocarbon, (iii) aliphatic paraffinic $C_2$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %.

The feed's non-aromatic hydrocarbon can include $C_3$ and/or $C_4$ hydrocarbon e.g., (i) ≥20 wt. % propane, such as ≥40 wt. %, or ≥60 wt. %, and/or (ii) ≥20 wt. % butanes, such as ≥40 wt. %, or ≥60 wt. %. Although the feed's non-aromatic hydrocarbon can include $C_{5+}$ non-aromatic hydrocarbon, the amount when present is typically small, e.g., ≤20 wt. %, such as ≤10 wt. %, or ≤01 wt. %. Typically, the feed's non-aromatic hydrocarbon includes ≤10 wt. % of $C_{6+}$ saturated hydrocarbon, e.g., ≤5 wt. %. In certain aspects, the feed comprises ≥0.1 wt. % of $CO_2$ and ≥1 wt. % ethane, based on the weight of the feed. For example, the feed's non-aromatic hydrocarbon can comprise ≥5 wt. % ethane, such as ≥10 wt. %, or ≥25 wt. %, or ≥50 wt. %, or ≥75 wt. %, or ≥90 wt. %, or ≥95 wt. %, or in the range of from 1 wt. % to 95 wt. %, or from 5 wt. % to 50 wt. %, or from 10 wt. % to 40 wt. %. One representative feed comprises ≥1 wt. % of $CO_2$ and (i) ≥10 wt. % ethane, such as in the range of from 10 wt. % to 40 wt. %; and further comprises (ii) 1 wt. % to 40 wt. % methane, (iii) 20 wt. % to 50 wt. % propane, and (iv) 20 wt. % to 50 wt. % butanes. In other aspects, $A_{1F}$ is <1 wt. %, e.g., ≤0.1 wt. %, or ≤0.1 wt. %.

Optionally, the feed contains unsaturated $C_{2+}$ hydrocarbon, such as $C_2$-$C_5$ Unsaturated hydrocarbon. When present, the amount of $C_{2+}$ unsaturated hydrocarbon is typically ≤20 wt. %, e.g., ≤10 wt. %, such as ≤1 wt. %, or ≤0.1 wt. %, or in the range of from 0.1 wt. % to 10 wt. %. The feed can be substantially-free of non-aliphatic hydrocarbon. More particularly, the feed can be substantially-free of aromatic hydrocarbon, where substantially-free in this context means <1 wt. % based on the weight of the feed, such as ≤0.1 wt. %, or ≤0.01 wt. %, or ≤0.001 wt. %. One representative feed comprises ≥1 wt. % of $CO_2$; <1 wt. % ethane; ≤1 wt. % of aromatic hydrocarbon; and ≥1 wt. % of $C_{3+}$ paraffinic hydrocarbon, e.g., ≥10 wt. % of a mixture of $C_3$ and $C_4$, such as ≥50 wt. %, or ≥75 wt. %, or in the range of 80 wt. % to 99 wt.%. Another representative feed comprises ≥1 wt. % of $CO_2$; 10 wt. % to 40 wt. % ethane; 20 wt. % to 50 wt. % propane, and 20 wt. % to 50 wt. % butanes, and further comprises 1 wt. % to 40 wt. % methane and ≤1 wt. % of aromatic hydrocarbon.

Besides $CO_2$ and non-aromatic hydrocarbon, the feed can further include one or more optional components, e.g., one or more of impurities, molecular hydrogen, and diluent. Typical impurities include CO, $H_2S$, and mercaptan. When the feed includes impurities, the amount is typically small, e.g., ≤10 wt. % based on the weight of the feed, such as ≤1 wt. %, or ≤0.1 wt. %. When the feed comprises molecular hydrogen, the amount of molecular hydrogen is typically ≤1 wt. %, based on the weight of the feed, such as ≤0.1 wt. %. When the feed includes diluent, the diluent can be present in the feed's source material (e.g., methane in natural gas) and/or diluent added to the feed are within the scope of the invention. The amount of diluent in the feed is typically ≤60 wt. %, based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified first and second catalysts, e.g., methane, molecular nitrogen, and inert atomic gasses such as argon. When the diluent is methane, the methane typically is present in the feed in an amount ≥1 wt. %, such as ≥10 wt. %, or ≥20 wt. %, or ≥60 wt. %. Even though methane is a diluent, i.e., it typically does not react to produce aromatic hydrocarbon or catalyst coke in the presence of the specified dehydrocyclization catalyst under the specified reaction conditions, its presence is beneficial. It is believed that this benefit results at least in part from a decrease in the partial pressure of the feed's non-aromatic hydrocarbon that is achieved when the feed includes methane as diluent. Decreasing the partial pressure of the feed's non-aromatic hydrocarbon, particularly the partial pressure of the feed's $C_2$-$C_5$ hydrocarbon, has been found to lessen the amount of catalyst coke formed under the specified dehydrocyclization process conditions.

The feed's light hydrocarbon can be obtained from natural and/or synthetic sources. For example, the feed can be obtained from natural hydrocarbon sources including those associated with producing petroleum. Synthetic hydrocarbon sources include, e.g., streams obtained from refining and petrochemical plants. Synthetic hydrocarbon sources also include those in which hydrocarbon within a geological formation has been purposefully subjected to one or more chemical transformations. Synthetic hydrocarbon sources also include process recycle streams, e.g., a portion of the product obtained from dehydrocyclization and/or $CO_2$ conversion. Such recycle, when used, can include, e.g., one or more of methane, molecular hydrogen, and $C_{2+}$ non-aromatic hydrocarbon, typically $C_2$ to $C_5$ hydrocarbon. When less than the desired amount of $CO_2$ is present in a natural or synthetic source, additional $CO_2$ can be added from an additional source as needed.

In certain aspects, the source of light hydrocarbon includes natural gas, e.g., raw natural gas. Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more of petroleum deposits, coal deposits, and shale deposits. Natural gas produced by conventional production methods is suitable, but the invention is not limited thereto. The natural gas can be a raw gas, namely one that is obtained from a geologic formation without intervening processing (such as fractionation with reflux), except for treatments to (i) adjust the amount of $CO_2$ in the feed, (ii) remove impurities such as water and/or any other liquids, mercaptans, hydrogen sulfide, carbon dioxide; and (iii) adjust the relative amounts of non-aromatic hydrocarbon in the feed (typically by separating $C_{4+}$ hydrocarbon in one or more vapor-liquid separators). Conventional methods can be used for removing impurities and/or adjusting the relative amount of the non-aromatic hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas has a non-aromatic hydrocarbon component comprising 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises a natural gas which includes ≥1 wt. % of $C_{2+}$ non-aromatic hydrocarbon and ≥0.005 wt. % of $CO_2$, such as raw natural gas, e.g., ≥75 wt. %, or ≥90 wt. %, or ≥95 wt. %.

Any form of raw gas can be used as a source material, although those containing an appreciable amount of $CO_2$ (e.g., ≥0.05 wt. % of $CO_2$, such as ≥0.5 wt. %, or ≥1 wt. %, or ≥5 wt. %) are particularly useful. The raw gas can be, e.g., one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.1-1 (0.09) |

In certain aspects, the feed comprises ≥75 wt. % (based on the weight of the feed) of Associated Gas having a $CO_2$ content ≥0.05 wt. % (based on the weight of the associated gas), e.g., ≥90 wt. % of Associated Gas, such as ≥95 wt. %. Associated Gas is typically found with petroleum deposits, e.g., dissolved in the oil or as a free "gas cap" above the oil in a reservoir. In conventional petroleum production, the lack of effective natural transportation facilities, e.g., the lack of natural gas liquefaction and/or pipeline facilities, can result in Associated Gas being stranded at or near the reservoir. This in turn can lead to a need for undesirable natural gas flaring. Moreover, even in locations where pipeline facilities are available, Associated Gas may be excluded from the pipeline because it typically exceeds one or more pipeline specifications, e.g., ≤12 wt. % ethane, ≤5 wt. % propane, ≤2 wt. % butanes, a Wobbe Index of from 49.01 $MJ/sm^3$ to 52.22 $MJ/sm^3$, and a heating value of from 36.07 $MJ/sm^3$ to 41.40 $MJ/sm^3$.

The invention is advantageous in remote or under-developed locations, where (i) the lack of cryogenic methane separation facilities and/or $CO_2$ separations facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline.

The feed is exposed to the first catalyst under conversion conditions effective for (i) converting ≥10 wt. % of the feed's $C_{2+}$ non-aromatic hydrocarbon to aromatic hydrocarbon and molecular hydrogen. Aromatic hydrocarbon yield is increased by reacting ≥1 wt. % of the feed's $CO_2$ with at least a portion of the molecular hydrogen in the presence of the second catalyst to produce methane and water, which can be separated from the aromatic hydrocarbon. Certain aspects of the first and second catalysts will now be described in more detail. The invention is not limited to these aspects, and this description is not meant to foreclose other aspects of these catalysts within the broader scope of the invention.
Representative Catalysts Typically, the first catalyst (the dehydrocyclization catalyst) includes ≥10 wt. % of a molecular sieve component and ≥0.005 wt. % of a dehydrogenation component. For example, the first catalyst can comprise ≥50 wt. % of the molecular sieve component and at least 1 wt. % of the dehydrogenation component.

When the first catalyst's molecular sieve component and dehydrogenation component together include less than 100 wt. % of the catalyst, ≥90 wt. % of the remainder can include a matrix component, such as ≥99 wt. % of the remainder. The first catalyst typically includes the molecular sieve component in an amount ≥20 wt. %, based on the weight of the first catalyst, e.g., ≥25 wt. %, such as in the range of from 30 wt. % to 99.9 wt. %. The molecular sieve typically has a Constraint Index in the range of about 1-12. In certain aspects, the molecular sieve component includes aluminosilicate, e.g., ≥90 wt. % of at least one aluminosilicate. The aluminosilicate can be an un-substituted aluminosilicate, a substituted aluminosilicate, or a combination thereof. For example, the aluminosilicate can be in a form where at least a portion of its original metal has been replaced, e.g., by ion exchange, with other suitable metal (typically metal cation) of Groups 1-13 of the Periodic Table. Typically, the aluminosilicate includes zeolite aluminosilicate, e.g., ≥90 wt. % of at least one zeolite based on the weight of the aluminosilicate. Zeolite can have at least part of its aluminum is replaced by a different trivalent metal, such as gallium or indium.

The molecular sieve component typically includes ≥90 wt. % of one or more of the specified molecular sieves, e.g., ≥95 wt. %. In certain aspects, the molecular sieve component includes at least one zeolite molecular sieve, e.g., ≥90 wt. % zeolite, such as ≥95 wt. %, based on the weight of the molecular sieve component. The molecular sieve component can consist essentially of zeolite, consist of zeolite, or can include zeolite in combination with other (e.g., non-zeolitic) molecular sieve. The zeolite can be in hydrogen form, e.g., zeolite synthesized in the alkali metal form and then converted to the hydrogen form. Typically the zeolite has a medium pore size and a Constraint Index of 2-12 (as defined in U.S. Pat. No. 4,016,218). Optionally, the zeolite has at least one set of pores of substantially uniform size extending through the molecular sieve, wherein geometric mean of the cross-sectional dimensions of each of the sets of pores is >5 Å, or >5.3 Å, e.g., ≥5.4 Å such as ≥5.5 Å, or in the range of 5 Å to 7 Å, or 5.4 Å to 7 Å. Examples of suitable zeolites include ZSM-5 (including H-ZSM-5), ZSM-11, ZSM-12, ZSM-22, ZSM-23, ZSM-35, and ZSM-48, including and mixtures and intermediates thereof such as ZSM-5/ZSM-11 admixture. For example, the molecular sieve component can include ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 micrometers (µm), such as in the range of 0.02 µm to 0.05 µm. Small crystal ZSM-5 and the method for determining molecular sieve crystal size are disclosed in U.S. Pat. No. 6,670,517, which is incorporated by reference herein in its entirety.

In other aspects, the molecular sieve component includes at least one molecular sieve of the MCM-22 family (including mixtures of MCM-22 family molecular sieve), e.g., MCM-22 alone or in combination with other molecular sieve such as one or more of the specified zeolites. The MCM-22 family includes those molecular sieves having an X-ray diffraction pattern including d-spacing maxima (in Å) at 12.4±0.25, 6.9±0.15, 3.57±0.07 and 3.42±0.07. Examples of suitable MCM-22-family molecular sieve are disclosed in U.S. Pat. Nos. 4,954,325; 4,439,409 (PSH-3); U.S. Pat. No. 4,826,667 (SSZ-25); U.S. Pat. No. 6,077,498 (ITQ-1); U.S.

Pat. No. 5,250,277 (MCM-36); U.S. Pat. No. 5,236,575 (MCM-49); and U.S. Pat. No. 5,362,697 (MCM-56); European Patent No. 0293032 (UZM-8, ERB-1); and P.C.T. Patent Application Publication No. WO 97/17290 (ITQ-2).

When the molecular sieve component includes at least one aluminosilicate, e.g., ≥90 wt. % aluminosilicate, the aluminosilicate's silica:alumina ratio (substantially the same as the aluminosilicate's Si:Al$_2$ atomic ratio) is typically ≥2, e.g., in the range of from 5 to 100, such as from 10-80. The silica:alumina ratio is meant to represent the Si:Al$_2$ atomic ratio in the rigid anionic framework of the crystalline aluminosilicate. Alternatively or in addition, the first catalyst can be made more resistant to deactivation (and increase aromatic hydrocarbon yield) by including phosphorous with the molecular sieve component. The amount of phosphorous can be ≥1 wt. %, based on the weight of the molecular sieve component. For example, when the molecular sieve component includes aluminosilicate, the phosphorous:aluminum atomic ratio can be in the range of from 0.01 to 1. Aluminosilicate having a greater silica:alumina ratio can be utilized when a lower catalyst acidity is desired, e.g., in the range of from 44 to 100, such as from 50 to 80, or 55 to 75.

In addition to the molecular sieve component, the first catalyst includes ≥0.005 wt. %, based on the weight of the catalyst, of a dehydrogenation component, e.g., at least one dehydrogenation metal. The dehydrogenation component can include one or more neutral metals selected from Groups 3 to 13 of the Periodic Table, such as one or more of Ga, Zn, Mo, W, La, Pt, and Pd, and/or one or more oxides, sulfides and/or carbides of these metals. For example, the dehydrogenation component can be one or more of Ga, Zn, Mo, W, and La. In particular aspects, the dehydrogenation component comprises Ga and/or Zn.

Typically, the dehydrogenation component includes ≥90 wt. % of the one or more of the specified dehydrogenation metals and/or oxide thereof, e.g., ≥95 wt. %, or ≥99 wt. %. For example, the dehydrogenation component can include ≥90 wt. % of (A) Ga and/or (B) Zn, including oxides thereof. Typically, the catalyst includes ≥0.01 wt. % of the dehydrogenation component, based on the weight of the catalyst, e.g., ≥0.1 wt. % of the dehydrogenation component, such as ≥0.5 wt. %, or ≥1 wt. %.

When the dehydrogenation component has a greater catalytic dehydrogenation activity, e.g., Pt, and/or Pd, a lesser amount of dehydrogenation component is needed, e.g., in the range of 0.005 wt. % to 0.1 wt. %, based on the weight of the first catalyst, such as 0.01 wt. % to 0.6 wt. %, or 0.01 wt. % to 0.05 wt. %. When the dehydrogenation component has a lesser dehydrogenation activity, e.g., one or more of Ga, Zn, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

The dehydrogenation component can be provided on, in, or proximate to the first catalyst in any manner, for example by conventional methods such as impregnation or ion exchange. At least part of the dehydrogenation metal may also be present in the crystalline framework of the molecular sieve. For one representative catalyst, (i) the dehydrogenation component includes ≥95 wt. % of (A) Ga and/or (B) Zn, and (ii) the first molecular sieve component includes ≥95 wt. % of H-ZSM-5.

In certain aspects, the first catalyst's dehydrogenation component includes ≥99 wt. % of one or more of Ga, Zn, and In, and the molecular sieve component includes ≥99 wt. % of ZSM-5-type zeolite that has been impregnated with the dehydrogenation metal component and/or ion exchanged with the dehydrogenation metal component. For example, the first catalyst can include Ga-impregnated and/or In-impregnated H-ZSM-5, Ga-exchanged and/or In-exchanged H-ZSM-5, H-gallosilicate of ZSM-5 type structure and H-galloaluminosilicate of ZSM-5 type structure. Optionally, the first catalyst includes (i) tetrahedral aluminum and/or gallium, which is present in the zeolite framework or lattice, and/or (ii) octahedral gallium or indium, which is not present in the zeolite framework but present in the zeolite channels in close vicinity to the zeolitic protonic acid sites. While not wishing to be bound by any theory or model, the tetrahedral or framework Al and/or Ga is believed to contribute to an acid function of the first catalyst, and octahedral or non-framework Ga and/or In is believed to contribute to the dehydrogenation function of the first catalyst. Although typically the zeolite is impregnated or ion-exchanged with the dehydrogenation metal, other forms of zeolite can be used, such as H-galloaluminosilicate of ZSM-5 type structure having framework (tetrahedral) Si/Al and Si/Ga atomic ratios of about 10:1 to 100:1 and 15:1 to 150:1, respectively, and non-framework (octahedral) Ga of about 0.5 wt. % to 0 wt. %.

Besides the molecular sieve component and dehydrogenation component, the first catalyst can further include an optional matrix component, e.g., one or more inorganic binders. The amount of matrix component is not critical, and can be in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture.

Alternatively or in addition, the matrix component can include one or more substantially inactive materials. Inactive materials typically serve as diluents to control the amount of dehydrocyclization, either alone or with other means for controlling the dehydrocyclization reaction rate. Alternatively or in addition to any phosphorous added to or impregnated into the molecular sieve component, the matrix component can optionally include phosphorous, e.g., to lessen catalyst acidity. Lessening catalyst acidity typically decreases the amount of catalyst coke produced during dehydrocyclization. Suitable phosphorous-containing matrices are disclosed in U.S. Pat. No. 5,026,937, which is incorporated by reference herein in its entirety. In certain aspects, the first catalyst is substantially-free of matrix, e.g., contains ≤1 wt. % of matrix, such as ≤0.1 wt. %. In particular, the catalyst can be substantially free of binder, e.g., contains ≤1 wt. % of binder, such as ≤0.1 wt. %. For example, the first catalyst's molecular sieve component can includes ≥95 wt. % of substantially binder-free bound molecular sieve, e.g., ≥95 wt. % of substantially binder-free ZSM-5, and in particular small crystal H-ZSM-5.

The first catalyst can be subjected to one or more treatments, e.g., a selectivation treatment to increase selectivity for producing desired aromatic hydrocarbon compounds such as para-xylene. For example, the selectivation can be carried out before introduction of the first catalyst into the reactor and/or in-situ in the reactor, e.g., by contacting the catalyst with a selectivating agent, such as at least one organosilicon in a liquid carrier and subsequently calcining the first catalyst at a temperature of 350° C. to 550° C. This selectivation procedure can be repeated two or more times and alters the diffusion characteristics of the catalyst such that the formation of para-xylene over other xylene isomers is favored. Such a selectivation process is described in detail in U.S. Pat. Nos. 5,633,417 and 5,675,047.

Typically, the first catalyst has a surface area as measured by nitrogen physisorption in the range of from 100 m$^2$/g to 600 m$^2$/g, e.g., in the range of from 200 m$^2$/g to 500 m$^2$/g. When the catalyst includes aluminosilicate which includes phosphorous, the phosphorous:aluminum atomic ratio is typically in the range of from 0.01 to 0.5. For example, the first catalyst can contain ≥10 wt. % of phosphorous-modified alumina, such as ≥15 wt. %, or in the range of from 10 wt. % to 20 wt. %.

Certain aspects of the invention include exposing the specified feed to the specified first catalyst under conversion conditions effective for (i) converting ≥10 wt. % of the feed's $C_{2+}$ non-aromatic hydrocarbon to aromatic hydrocarbon and molecular hydrogen. Aromatic hydrocarbon yield is increased by reacting at least a portion of the feed's $CO_2$ with at least a portion of the molecular hydrogen produced by the dehydrocyclization in the presence of the second catalyst to produce methane and water. The second catalyst (the $CO_2$ conversion catalyst) typically comprises ≥0.005 wt. % of a $CO_2$ conversion component, e.g., or more of Ru, Rh, Ni, Co, and Fe. For example, the second catalyst can comprise ≥0.1 wt. % of the $CO_2$ conversion component, wherein the $CO_2$ conversion component includes ≥90 wt. % of one or more of Ru, Rh, and Ni. In particular aspects, the second catalyst includes ≥1 wt. % of the $CO_2$ conversion component, the $CO_2$ conversion component comprises ≥95 wt. % of (i) Ru and/or (ii) Ni. Although it can consist essentially of or consist of the $CO_2$ conversion component, second catalysts which include additional components are within the scope of the invention. For example, the second catalyst can further comprise a support material, typically one or more inorganic oxide. In certain aspects, the second catalyst comprises ≥1 wt. % of the $CO_2$ conversion component and further comprises an inorganic oxide support, e.g., ≥1 wt. % of one or more of oxide of chromium, oxide of aluminum, oxide of magnesium, oxide of manganese, oxide of cerium, oxide of zirconium, oxide of titanium, and oxide of thorium. Although the second catalyst can optionally include matrix and/or binder, typically these are not used. For example, certain forms of the second catalyst contain ≤0.1 wt. % of binder.

In one form, the first and second catalysts are individual catalysts located in separate catalyst beds, e.g., with an initial dehydrocyclization occurring in a first catalyst bed of the specified first catalyst. At least a portion of the molecular hydrogen produced in the vicinity of the first catalyst bed during the initial dehydrocyclization is reacted under $CO_2$ conversion conditions with at least a portion of the feed's $CO_2$ to produce methane and water. The $CO_2$ conversion can be carried out using the specified second catalyst in particulate form located in a second bed positioned downstream of the first bed. Additional aromatic hydrocarbon can then be produced by a second dehydrocyclization, which includes dehydrocyclizing at least a portion of (i) unreacted $C_{2+}$ non-aromatic hydrocarbon of the feed remaining downstream of the first bed and (ii) $C_{2+}$ hydrocarbon produced upstream of the second bed, e.g., by a hydrogenolysis side reaction in the first bed. The second dehydrocyclization reaction, which produces the additional aromatic hydrocarbon, can be carried out using a third catalyst selected from among the same compositions as the first catalyst. For example, in certain aspects the initial dehydrocyclization is carried out in the presence of the specified first catalyst in particulate form and the second dehydrocyclization is carried out in the presence of a third catalyst (also in particulate form) that is of substantially the same composition as that of the first catalyst used for the initial dehydrocyclization. In other aspects, the first and third catalysts have different compositions, although both compositions are selected from among the compositions specified for the first catalyst. Typically, the third catalyst is located in a third catalyst bed positioned downstream of the second catalyst bed. Additional catalyst can be used, e.g., catalyst active for carrying out RWGS. The additional catalyst can be located in one or more beds of the dehydrocyclization catalyst, in one or more beds of the $CO_2$ conversion catalyst, or in additional beds located between beds of dehydrocyclization and $CO_2$ conversion catalyst.

Alternatively, or in addition, an active material in the form of a mixture of the first and second catalyst (e.g., particles of the first catalyst physically mixed with particles of the second catalyst) can be located in one or more catalyst beds for carrying out both dehydrocyclization and $CO_2$ conversion. The active material can comprise, e.g., (a) ≥10 wt. % of the specified first catalyst and ≥10 wt. % of the specified second catalyst. The catalytic action of the active material can be used to perform the initial dehydrocyclization, the $CO_2$ conversion, and the second dehydrocyclization. For example, the first catalyst can have the form of a first particulate, the second catalyst can have the form of a second particulate, the active material has the form of a mixture of the first and second particulates, and the active material comprises ≥20 wt. % of the first catalyst and ≥20 wt. % of the second catalyst. The active material optionally contains additional catalyst, e.g., RWGS catalyst.

Alternatively or in addition, the active material can be in the form of a catalytic composite, e.g., a solid composite composition in the form of a particulate, with the initial dehydrocyclization, the $CO_2$ conversion, and the second dehydrocyclization being carried out proximate to at least one bed of the catalyst composite. In one form, the catalyst composite includes ≥10 wt. % of the specified first catalyst and ≥10 wt. % of the specified second catalyst, e.g., ≥20 wt. % of the first catalyst and ≥20 wt. % of the second catalyst. The composite optionally contains additional catalyst, e.g., RWGS catalyst.

Conventional methods can be used to produce the active material, but the invention is not limited thereto. For example, the active material can be made from starting materials which include (a) molecular sieve having a Constraint Index in the range of from 1 to 12; (b) a first precursor comprising a dehydrogenation component which includes one or more of Ga, Zn, Mo, W, La, Pt, and Pd; (c) oxide matrix which includes one or more of oxide of chromium, oxide of aluminum, oxide of magnesium, oxide of manganese, oxide of cerium, oxide of zirconium, oxide of titanium, and oxide of thorium; and (d) a second precursor comprising a $CO_2$ conversion component which includes one or more of Ru, Rh, Ni, Co, and Fe. The method for making the catalytic composite includes contacting the molecular sieve and the first precursor under conditions effective for transferring to the molecular sieve at least a portion of the dehydrogenation component to produce a loaded molecular sieve comprising ≥0.005 wt. % of one or more of Ga, Zn, Mo, W, La, Pt, and Pd. The method also includes contacting the matrix and the second precursor under conditions effective for transferring to the matrix at least a portion of the $CO_2$ conversion component to produce a loaded matrix comprising ≥0.005 wt. % of one or more of Ru, Rh, Ni, Co, and Fe. The loaded molecular sieve can be calcined to produce a calcined loaded molecular sieve, and the loaded matrix can be calcined to produce a calcined loaded matrix. The first catalyst can be produced by reducing the calcined loaded molecular sieve. The second catalyst can be produced by reducing the calcined loaded matrix. One or more of the loaded molecular sieve, the calcined loaded molecular sieve, the first catalyst, the loaded matrix, the calcined loaded matrix, and the second catalyst can be in the form of a particulate. The active material can be produced by combining the first and second catalysts, e.g., by mixing. Alternatively or in addition, the active material can be produced by (i) combining the loaded molecular sieve and loaded matrix, and then carrying out the calcining and reducing or (ii) calcining the loaded molecular sieve and calcining the loaded matrix, combining the products of these calcinations, and then reducing the combined products. In alternative aspects, a matrix is not used, and the active material is produced by contacting the molecular sieve with the first and second precursors (simultaneously, or one before the other) in order to produce a loaded molecular sieve comprising ≥0.005 wt. % of one or more of Ga, Zn, Mo, W, La, Pt, and Pd transferred from the first precursor and ≥0.005 wt. % of one or more of transferred Ru, Rh, Ni, Co, and Fe transferred from the second precursor. Calcining and reducing can be carried out as in the preceding aspects. The alternative aspects can be particularly useful for producing the active material in the form of a catalytic composite. Examples of suitable conventional methods for applying catalytic metals to zeolite, for calcining the loaded zeolite, and for reducing the calcined zeolite are disclosed in S. Yamaouchi, et al., Sekiyu Gakkaishi, 37, 3, 278-284, 1994.

Representative Dehydrocyclization and Aromatization Reactions

The dehydrocyclization and $CO_2$ conversion reactions can be carried out by exposing the feed to one or more beds containing catalytically effective amounts of the first and second catalyst under conditions effective for catalytic dehydrocyclization and catalytic $CO_2$ conversion. A feature of the invention is that substantially the same conditions can be used for dehydrocyclization and $CO_2$ conversion. Accordingly, when one catalyst bed is used, e.g., a catalyst bed containing the specified active material, process conditions can be selected so that both dehydrocyclization and $CO_2$ conversion are effectively carried out. Representative process conditions include a temperature in range of from 400° C. to 700° C., a pressure ≥10 psia (68.9 kPa), and a WHSV in the range of 0.1 $hr^{-1}$ to 20 $hr^{-1}$. Another feature of the invention is that the presence of the second catalyst allows for carrying out the dehydrocyclization at a lower temperature (e.g., 50° C. lower, or even 100° C. lower, with substantially the same yield of aromatic hydrocarbon). Doing so beneficially decreases the rate of catalyst deactivation, as compared with processes utilizing substantially the same feed and substantially the same first catalyst but not the specified second catalyst. Those skilled in the art will appreciate that the specified temperature represents average temperatures across the catalyst bed. Average temperature is calculated by adding the bed's inlet temperature to the bed's outlet temperature, and then dividing the sum by 2. The specified pressure is not an average pressure. Instead, the specified pressure corresponds to that subsisting at the bed's inlet. Fixed catalyst beds, moving catalyst beds, fluidized catalyst beds, ebullating catalyst beds, combinations thereof, etc., are all within the scope of the invention.

In certain aspects, the reactions are carried out in a plurality of catalyst beds, which can be located in one or more reactors. The plurality of beds can have the form of alternating catalyst beds of (i) one or more compositions and/or forms of the dehydrocyclization catalyst and (ii) one or more compositions and/or forms of the second $CO_2$ conversion catalyst, one after the other. Other aspects use (i) a first catalyst bed which includes the first catalyst for the initial dehydrocyclization, (ii) a second catalyst bed located downstream of the first catalyst bed, the second catalyst bed containing the second catalyst for carrying out $CO_2$ conversion, and (iii) a third bed located downstream of the second bed, the third bed containing the third catalyst for carrying out additional dehydrocyclization. Optionally, a fourth catalyst bed is located downstream of the third catalyst bed, where the fourth catalyst bed contains (A) a catalytic composition selected from among the same compositions specified for the first and/or second catalyst or (B) the specified active material. The fourth catalysts bed produces more additional aromatic hydrocarbon, in addition to those produced in the third bed. In yet other aspects, a first bed containing the specified active material (which can be in composite form) is located upstream of a second catalyst bed which contains (A) a catalytic composition selected from among those specified for the first catalyst, for additional dehydrocyclization, or (B) a catalytic composition selected from among those specified for the second catalyst, for additional $CO_2$ conversion. Additional catalyst beds can be located downstream of the second bed for further $CO_2$ conversion and further dehydrocyclization, e.g., alternating beds of catalyst having these functionalities. Further aspects include first and second beds, where the first bed contains a catalytically active composition selected from among those specified for the active material (optionally in composite form) and the second bed contains a second catalytically active composition that is also selected from among those specified for the active material (optionally in composite form). In these aspects, aromatics yield is increased by producing aromatic hydrocarbon in the first catalyst bed, additional aromatic hydrocarbon in the first catalyst bed (as a result of molecular hydrogen consumption during $CO_2$ methanation), and more additional aromatic hydrocarbon in the second bed.

When more than one catalyst bed is used, all of the catalyst beds can be located in a single reactor vessel, but this is not required. For example, a first bed of the first catalyst can be located upstream of a second bed of the second catalyst, with both beds located in a first reactor vessel, with at least a portion of the heat released by the exothermic $CO_2$ conversion reaction being utilized by the endothermic dehydrocyclization reaction in the first catalyst bed. Reaction product from the first vessel can be conducted to a second vessel, the second vessel containing a third catalyst bed which includes the specified first catalyst and/or the specified active material for additional dehydrocyclization and, optionally, additional $CO_2$ conversion. Although it is not required, one or more separations can be carried out, e.g., between catalyst beds, such as between the first and second vessels. For example one or more of the following can be separated from the aromatic effluent of the first vessel (the "first product") upstream of the second vessel: excess molecular hydrogen, excess $CO_2$, excess methane, excess $C_{2+}$ non-aromatic hydrocarbon, and excess aromatic hydrocarbon. Likewise, one or more heat transfer stages can be located between the first and second vessels for adding or removing heat from the product of the first vessel.

Particular aspects of the invention which utilize at least first and second catalyst beds will now be described in more detail. The invention is not limited to these aspects, and this description is not meant to foreclose other aspects within the broader scope of the invention. The first catalyst bed can include the specified active material. In aspects where substantially all of the feed's $CO_2$ is consumed by $CO_2$ conversion in the first catalyst bed, the second catalyst bed generally includes a catalytic composition selected from among those specified for the first catalyst. When the first product includes greater than about 0.1 wt. % of unreacted feed $CO_2$ and/or added $CO_2$, the second catalyst bed typically includes a catalytic composition selected from among those specified for the active material, which can be different from the catalytic composition of the first catalyst bed.

When first and second catalyst beds are used, the first catalyst bed can be located within a reaction zone positioned in a first reaction vessel ("first reactor"), with the second catalyst bed located within a reaction zone positioned in a second reaction vessel. The specified feed is conducted to the inlet of the first reactor for carrying out the specified dehydrocyclization and $CO_2$ conversion reactions. Aromatic hydrocarbon yield is observed to be greater than when utilizing a catalytic composition that does not include a $CO_2$ methanation component. The first product is conducted away from the outlet of first reactor to the inlet of the second reactor. The first product typically comprises unreacted $C_{2+}$ non-aromatic hydrocarbon, additional non-aromatic hydrocarbon (produced, e.g., by hydrogenolysis), optionally at least a portion of the molecular hydrogen produced during the dehydrocyclization, and optionally at least a portion of unreacted feed $CO_2$.

Process conditions in the first reactor can include exposing the feed to a temperature $T_1$ in the range of from 400° C. to 630° C., and a pressure $P_1$ that is sufficient for carrying out the dehydrocyclization. Typically, $T_1$ is in the range of from 450° C. to 605° C. Typically, $P_1$ is ≥20 psia (137.9 kPa) e.g., ≥35 psia (241.3 kPa), such as in the range of from 35 psia (241.3 kPa) to 300 psia (2070 kPa). For example, $P_1$ can be in the range of from 35 psia (241.3 kPa) to 300 psia (2070 kPa), such as 37 psia (255.1 kPa) to 80 psia (522 kPa), or 40 psia (275.8 kPa) to 80 psia (522kPa), or 45 psia (310.2 kPa) to 80 psia (522kPa). Generally, the conditions further include a WHSV in the range of from 0.1 $hr^{-1}$ to 20 $hr^{-1}$, e.g., 0.2 $hr^{-1}$ to 5 $hr^{-1}$, such as 0.3 $hr^{-1}$-to 1.0 $hr^{-1}$. It has been found that when these conditions are used with the specified $CO_2$ conversion catalyst, the $CO_2$ conversion has a greater selectivity for methane than CO, e.g., ≥10% greater selectivity for methane, such as ≥25% greater selectivity. Since the $CO_2$ conversion is exothermic and the dehydrocyclization is endothermic, the average temperature across the reaction zone within the first reactor (and across the first catalyst bed) is typically ≤600° C., more typically in the range of from 20° C. to 200° C., e.g., in the range of from 50° C. to 150° C. Typically, the feed is not exposed to a temperature ≥630° C. at the inlet to the first catalyst bed. When the first reactor is used primarily for propane and/or butane aromatization, the presence of an active material having methanation functionality allows for the use of a lower $T_1$, e.g., in the range of from 400° C. to 550° C., as compared with conventional processes for propane and/or butane aromatization that do not utilize catalytic methanation. The specified process conditions have been found to be particularly effective for aromatizing feeds having a $C_{2+}$ non-aromatic hydrocarbon component containing ≥50 wt. % of paraffinic $C_2$-$C_4$ hydrocarbon. Those skilled in the art will appreciate that for particular feed $CO_2$ and $C_{2+}$ non-aromatic hydrocarbon contents, the relative amounts of first and second catalyst in the active material can be selected to prevent consumption in the first reactor of substantially all of the feed's $CO_2$ and/or of substantially all of the molecular hydrogen produced by the dehydrocyclization. Typically, the amount of feed $CO_2$ consumed in the first reactor will be in the range of from 10 wt. % to 90 wt. % based on the total weight of $CO_2$ in the feed, e.g., 20 wt. % to about 80 wt. %. Alternatively or in addition, $CO_2$ can be added to the first product, e.g., at a location upstream of the second vessel. The presence of unreacted (or added) $CO_2$ in the first product is optional but can be beneficial because (i) it can be exothermically reacted with molecular hydrogen produced during endothermic dehydrocyclization in the second reactor bed, which makes the second reactor more isothermal, and (ii) the presence of $CO_2$ has been found to stabilize certain first catalysts, particularly those which include Zn, in catalytically active form. While not wishing to be bound by any theory or model, the presence of unreacted molecular hydrogen throughout the first catalyst bed (evidence by the presence of unconsumed molecular hydrogen at the catalyst bed outlet) has been found to lessen the amount of catalyst coke accumulation, leading to increased reactor run lengths before catalyst regeneration is needed. For example, when unconsumed molecular hydrogen is present at the outlet of the first catalyst bed, and the process conditions include a pressure $P_1$≥35 psia (241.3 kPa, the reactions of the first catalyst bed can be sustained for a time duration ≥50 hours, e.g., ≥100 hours, such as ≥200 hours, or ≥500 hours with a decrease in the yield of $C_{6+}$ hydrocarbon of ≤10%, e.g., ≤5%, such as ≤1%. Regeneration can be carried out (regeneration mode operation) by halting feed flow to the first reactor off line and heating the first catalyst bed in the presence of at least one oxidant to remove at least a portion of any accumulated catalyst coke. The use of one or more substitute reactors (substantially similar to the first reactor) can be operated in parallel with the first reactor so the supply of first product is not interrupted when operating the first reactor or its substitute in regeneration mode. For example, when the first reactor is in regeneration mode, the substitute reactor can be converting the feed to the first product (reaction mode operation), and vice versa. The first reactor is typically operated in reaction mode for an average time duration ≥50 hours, e.g., ≥75 hours, such as ≥100 hours, or ≥120 hours, at an aromatics yield that is ≥75% of that attained at the start of reaction mode, e.g., ≥90%, such as ≥95%.

When the feed's $C_{2+}$ non-aromatic hydrocarbon component comprises ethane and $C_{3+}$ light hydrocarbon, the catalyst and conditions in the first reactor can be selected from among those specified to provide (i) ≤25 wt. % conversion of the feed's ethane, such as ≤10 wt. %, or ≤5 wt. %, or ≤1 wt. % and (ii) ≥25 wt. % conversion of the feed's $C_{3+}$, e.g., ≥50 wt. %, or ≥75 wt. %. Typically, one or more of the catalyst mass, catalyst volume, and feed flow rate are selected to achieve a $C_{3+}$ conversion (weight basis) ≥90%, such as ≥95%, or ≥98%. Although the first reactor dehydrocyclization reaction is selective for aromatic hydrocarbon, (i) ethane conversion products can also include methane and catalyst coke and (ii) $C_{3+}$ conversion products can also include ethane, methane, and catalyst coke. Accordingly, the amount of ethane in the first product can be considerably larger than that of the feed. Those skilled in the art will appreciate that within the ranges of process parameters specified for the first reactor, there are process conditions which result in a maximum propane conversion to aromatic hydrocarbon "$X_{MP}$". Unlike conventional multi-stage processes, the first reactor is typically operated at a propane conversion to aromatic hydrocarbon that is less than $X_{MP}$. Instead, when the feed to the first reactor comprises propane and/or when propane is produced in the first reactor, conditions are generally selected so that the initial (start of run) propane conversion to aromatic hydrocarbon in the first reactor "$X_{1P}$" is $\leq 0.95 \cdot X_{MP}$. Typically, $X_{1P} \leq 0.90 \cdot X_{MP}$, e.g., $\leq 0.85 \cdot X_{MP}$, or $\leq 0.80 \cdot X_{MP}$, or $\leq 0.75 \cdot X_{MP}$. It has been found that operating the first reactor under conditions which provide $X_{1P} \geq X_{MP}$ leads to excessive catalyst coking, typically resulting in a shortened cycle time in fixed bed operation. The same effect is observed for conversion of butanes to aromatic hydrocarbon, but with less sensitivity to changes in the first reactor's process conditions. Instead of operating at maximum conversion of butanes to aromatic hydrocarbon $X_{MB}$, the specified process conditions typically result in an initial (start of run) conversion of butenes to aromatic hydrocarbon ("$X_{1B}$") that is less than $X_{MB}$, e.g., $X_{1B} \leq 0.995 \cdot X_{MB}$, such as $\leq 0.99 \cdot X_{MB}$, or $\leq 0.985 \cdot X_{MB}$.

The first product is conducted away from the first reactor to the second reactor. Although not required, it is in the scope of the invention to conduct $\geq 50$ wt. % of the first product to the second reactor, e.g., $\geq 75$ wt. %, such as $\geq 90$ wt. %, or $\geq 99$ wt. %. In certain aspects, the first product is transferred to the second reactor with substantially no compositional adjustment. Typically, the first product comprises $\geq 90$ wt. % of the first reactor's effluent, e.g., $\geq 95$ wt. %, such as $\geq 99$ wt. %. Typically, at least 50 wt. % of the first product is conducted to the second reactor, e.g., $\geq 75$ wt. %, such as $\geq 90$ wt. %. Separation of first product components between the first and second reactors is generally not needed, although it within the scope of the invention. Optional separations include, e.g., separating and conducting away one or more of excess molecular hydrogen, excess $CO_2$, and excess methane. The term "excess" in this sense with respect to molecular hydrogen means more than is needed to lessen rate of catalyst coke accumulation in the second reactor, e.g., in the second catalyst bed. The term "excess" in this sense with respect to $CO_2$ means more than is needed to (i) decrease the temperature drop across the second catalyst bed into a desired range and/or (ii) more than is needed to stabilize the catalytic activity dehydrocyclization catalyst and/or the dehydrocyclization component of the active material in the second catalyst bed. The term "excess" in this sense with respect to methane means more methane than is needed for lessening the ethane partial pressure in the second reactor into a desirable range (which has been found to lessen the rate of catalyst coke accumulation). It is also within the scope of the invention to divide the entirety of first product into two or more streams, with one stream comprising $\geq 50$ wt. % of the entirety of the first product being conducted to the second reactor, e.g., $\geq 75$ wt. %, such as $\geq 90$ wt. %, or $\geq 95$ wt. %; and one or more additional streams being conducted away from the process. Typically, the portion of the first product that is reacted under dehydrocyclization conditions in the second reactor comprises $\geq 50$ wt. % of the first product's aromatic hydrocarbon, e.g., $\geq 75$ wt. %, such as $\geq 90$ wt. %, or $\geq 95$ wt. %; and $\geq 50$ wt. % of the first product's molecular hydrogen, such as $\geq 90$ wt. %, or $\geq 95$ wt. %. Typically, the portion of the first product that is reacted under dehydrocyclization conditions in the second reactor comprises $\geq 50$ wt. % of the first product's ethane, e.g., $\geq 75$ wt. %, such as $\geq 90$ wt. %, or $\geq 95$ wt. %; and $\geq 50$ wt. % of any other (i.e., besides ethane) non-aromatic hydrocarbon in the first product, e.g., $\geq 75$ wt. %, such as $\geq 90$ wt. %, or $\geq 95$ wt. %. Particularly when the feed's $C_{2+}$ non-aromatic hydrocarbon component includes $\geq 50$ wt. % of $C_2$-$C_4$ hydrocarbon, the first product or portion thereof conducted in to the second reactor contains $\geq 0.1$ wt. % ethane, e.g., $\geq 1$, such as $\geq 5$, or $\geq 10$.

Typically, the feed to the second reactor, e.g., the first product following any separations and/or any additions, includes $CO_2$ (unreacted feed $CO_2$ and/or added $CO_2$), e.g., $\geq 0.1$ wt. % $CO_2$, such as $\geq 1$ wt. %. In other aspects, the feed to the second reactor contains $>0.1$ wt. % of $CO_2$, e.g., $\leq 0.01$ wt. %, such as $\leq 0.001$ wt. %. When the feed to the second reactor includes $CO_2$, at least a portion of the heat needed for the dehydrocyclization of the first product's $C_{2+}$ non-aromatic hydrocarbon, particularly the first product's ethane, can be produced by the exothermic methanation of at least a portion of the $CO_2$. Typically, $\geq 50$ wt. % of the first product's $CO_2$ (and/or any added $CO_2$) is reacted to produce methane and water, where the $CO_2$ reacts with (i) molecular hydrogen present in the first product and/or (ii) molecular hydrogen produce during the dehydrocyclization in the second reactor, e.g., $\geq 75$ wt. %, such as $\geq 90$ wt. %. As in the first reactor, consuming molecular hydrogen by the methanation increases the yield of aromatic hydrocarbon produced by the dehydrocyclization reaction in the second reactor. Also as in the first reactor, varying the relative amount of first and second catalyst in the catalyst composition of the second bed can achieve the desired amount of $CO_2$ methanation and molecular hydrogen consumption over a wide variation in the amount of molecular hydrogen and the amount of $CO_2$ in the second reactor.

Process conditions in the second reactor typically include a temperature $T_2$ in the range of from 450° C. to 700° C., and a pressure $P_2 \leq 35$ psia (241.3 kPa). Typically, $T_1 \leq 0.9 \cdot T_2$, e.g., $T_1 \leq 0.85 \cdot T_2$, such as $T_1 \leq 0.8 \cdot T_2$. The pressure in the second reactor is typically less than that of the first reactor, e.g., $P_2 \leq 0.95 \cdot P_1$, such as $P_2 \leq 0.90 \cdot P_1$, or $P_2 \leq 0.85 \cdot P_1$, or $P_2 \leq 0.8 \cdot P_1$. Typically, reaction conditions include $T_2$ in the range of from 500° C. to 675° C. and $P_2 \leq 34$ psia (234.4 kPa), e.g., $\leq 32$ psia (220.6 kPa), such as $\leq 30$ psia (207 kPa), or in the range of from 10 psia (68.9 kPa) to 35 psia (241.3 kPa) or from 12 psia (82.8 kPa) to 34 psia (234.4 kPa). Generally, the reaction is carried out at a WHSV of the feed to the second reactor (e.g., the specified first product) in the range of from 0.1 hr$^{-1}$ to 20 hr$^{-1}$, e.g., 0.2 hr$^{-1}$ to 5 hr$^{-1}$, or 0.3 hr$^{-1}$ to 1 hr$^{-1}$. Those skilled in the art will appreciate that $T_2$ represents an average temperatures across the second catalyst bed. Average temperature is calculated by adding the bed's inlet temperature to the bed's outlet temperature, and then dividing the sum by 2. $P_2$ is not average pressure. Instead, it corresponds to the pressure at the inlet of the second catalyst bed. In a particular aspect, the average temperature across any reaction zone within the second reactor (and across any catalyst bed located within the second reactor) is $\leq 700$° C. Typically, the feed is not exposed to a temperature $\geq 700$° C. at the inlet to the second reactor bed. It has been found that when these conditions are used with the specified $CO_2$ conversion catalyst, the $CO_2$ conversion has a greater selectivity for methane (produced by methanation) than CO (produced by RWGS), e.g., $\geq 10\%$ greater selectivity for methane, such as $\geq 25\%$ greater selectivity. Unlike the first reactor, it has been found that increased reaction pressure in the second reactor (i) decreases the yield of aromatic hydrocarbon and (ii) increases the rate of catalyst coke accumulation. A $P_2 \leq 35$ psia (241.3 kPa) is generally needed to extend the duration of reaction mode operation to a time $\geq 50$ hours. As in the first reactor, the second reactor can be switched to regeneration mode operation to remove at least a portion of any accumulated catalyst coke. Also as in the case of the first reactor, one or more substitute reactors that are substantially similar to the second reactor can be used to prevent an interruption of the second product when the second reactor is in regeneration mode. The second reactor is typically operated in reaction mode for an average time duration ≥50 hours, e.g., ≥75 hours, such as ≥100 hours, or ≥120 hours, at an aromatics yield that is ≥95% of that attained at the start of dehydrocyclization mode, e.g., ≥90%, such as ≥75%. When the second reactor is used primarily for ethane aromatization in the presence of $CO_2$, the presence of an active material having catalytic methanation functionality allows for the use of a lower $T_2$, e.g., in the range of from 450° C. to 550° C., as compared with conventional processes for ethane aromatization that do not utilize a methanation.

Those skilled in the art will appreciate that within the ranges of conditions specified for the second reactor, there are process conditions which result in a maximum ethane conversion to aromatic hydrocarbon "$X_{ME}$". Unlike conventional multi-reactor processes, the second reactor typically is not operated at $X_{ME}$. Instead, process conditions are generally selected so that the initial (start of run) conversion of ethane to aromatic hydrocarbon in the second reactor "$X_{2E}$" is less than $X_{ME}$, e.g., ≤0.9·$X_{ME}$. Typically, $X_{2E}$≤0.85·$X_{ME}$, e.g., ≤0.8·$X_{ME}$, or ≤0.75·$X_{ME}$. It has been found that operating the second reactor under conditions which provide $X_{2E}$≥$X_{ME}$ lead to excessive catalyst coking, which typically necessitates a shortened duration of reaction mode operation, particularly in fixed bed operation. Since there is a net conversion of ethane in the second reactor, $X_{2E}$ is greater than zero. Generally, when operating under the specified conditions using the specified feeds, $X_{2E}$ is greater than the initial (start of run) conversion of ethane to aromatic hydrocarbon in the first reactor "$X_{1E}$". Typically, $[1-(X_{1E}/X_{2E})]$ is ≤5, e.g., ≤2, such as ≤1, or in the range of 0.5 to 5, or 0.6 to 2, or 0.6 to 1. Typically, ≥5 wt. % of the ethane present in the portion of the first product transferred to the second reactor is converted in the second reactor, e.g., ≥10 wt. %, such as ≥20 wt. %.

Contrary to expectations, it has been found that it is detrimental to operate the second reactor at a temperature sufficient for maximum conversion of the first product's ethane, typically $T_2$>700° C. Doing so is observed to result in a decrease in selectivity to the desired aromatic hydrocarbon product. It also has been found that operating the second reactor at a temperature >700° C. can lead to a chemical conversion of the catalyst's dehydrogenation component and a loss of catalytic dehydrocyclization activity, particularly when the dehydrogenation component comprises one or more oxide of Zn—although this effect is moderated when the first product that is transferred to the second reactor contains $CO_2$. While not wishing to be bound by any theory or model, it is believed that utilizing a temperature >700° C. results in a conversion from the oxide form to a metallic form of Zn, which has a greater vapor pressure than does the oxide form. The loss of catalytic dehydrocyclization activity is thus attributed at least partially to the evaporation of Zn from the catalyst. Typically, total ethane conversion in the second reactor is ≤60%, e.g., ≤50, such as ≤40%, or in the range of from 25% to 60%, or 30% to 55%, or 30% to 50%, or 30% to 40%.

The dehydrocyclization reaction and optional $CO_2$ conversion reaction in the second reactor produce more aromatic hydrocarbon, which is in addition to that produced in the first reactor. A second product is conducted away from the second reactor, the second product comprising (i) at least a portion of the aromatic hydrocarbon produced in the second reactor, (ii) at least an unconverted portion of any aromatic hydrocarbon that is introduced into the second reactor, methane, water, and optionally unconverted $C_{2+}$ non-aromatic hydrocarbon and/or unconverted $CO_2$. If desired, at least a portion of the second product's aromatic hydrocarbon can be separated and conducted away, i.e., for storage and/or further processing. Typically, the second product has a total aromatic hydrocarbon content of ≥5 wt. %, based on the weight of the second product, such as ≥10 wt. %, or in the range of from 1 wt. % to 95 wt. %, or 10 wt. % to 75 wt. %. The process produces a desirable BTX product. Even though $T_2$ is greater than $T_1$, it has been found that the second product has an unexpected increase in desirable xylene isomers, and an unexpected decrease yield of less desirable $C_{11+}$ aromatic hydrocarbon.

Although the catalyst used in the first reactor can be substantially the same as that used in the second reactor, typically the catalysts are different. For example, in certain aspects utilizing a feed comprising raw natural gas (<0.01 wt. % aromatic hydrocarbon), e.g., Associated Gas, the first reactor contains a first catalyst bed which includes Catalyst A and the second reactor contains a second catalyst bed which includes Catalyst B. Catalysts A and B will now be described in more detail.

Catalyst A is selected from among a subset of those compositions specified for the active material. Catalyst A, which can be in the form of a mixture or composite, includes (i) a dehydrocyclization component which comprises a molecular sieve component and a dehydrogenation component; and (ii) a $CO_2$ methanation component. The molecular sieve component comprises ≥90 wt. % of an aluminosilicate in hydrogen form, the aluminosilicate having a constraint index in the range of from 2-12 (e.g., phosphorous-modified H-ZSM-5) and a silica to alumina ratio in the range of from 50 to 80. The molecular sieve component can comprise ≥95 wt. % of substantially binder-free, small crystal H-ZSM-5. The dehydrogenation component comprises ≥90 wt. % of at least one oxide of Ga. Optionally, the dehydrogenation component further comprises matrix, e.g. ≥75 wt. % of alumina, silica, and combinations thereof. Optionally, the dehydrogenation component further comprises ≥1 wt. % phosphorus, e.g., in the form of phosphorous-modified H-ZSM-5 and/or by including phosphorous in the matrix component. The $CO_2$ methanation component comprises ≥90 wt. % of one or more of Ru, Rh, and Ni. Optionally, the $CO_2$ methanation component further comprises an inorganic oxide support, e.g., ≥1 wt. % of one or more of oxide of chromium, oxide of aluminum, oxide of magnesium, oxide of manganese, oxide of cerium, oxide of zirconium, oxide of titanium, and oxide of thorium.

Catalyst B is also selected from among a subset of those compositions specified for the active material. Like Catalyst A, Catalyst B can be in the form of a mixture or composite and includes (i) a dehydrocyclization component which comprises a molecular sieve component and a dehydrogenation component; and (ii) a $CO_2$ methanation component. The molecular sieve component comprises ≥90 wt. % of an aluminosilicate in hydrogen form, the aluminosilicate having a constraint index in the range of from 2-12 (e.g., small crystal H-ZSM-5) and a silica to alumina ratio in the range of from 3 to 60, e.g., from 10 to 40, such as from 15 to 35. The dehydrogenation component comprises ≥90 wt. % of (i) at least one oxide of Zn and/or (ii) at least one oxide of Ga. Optionally, the dehydrogenation component further comprises matrix, which when used typically comprises ≥90 wt.

% of alumina, silica, and combinations thereof. Catalyst B typically comprises <0.01 wt. % phosphorus.

Typically, Catalyst A and Catalyst B are each located in a plurality of fixed beds. Particularly in these aspects, the feed reacts in the presence of Catalyst A in the first reactor while exposed to a temperature $T_1$ in the range of from 450° C. to 605° C. and a pressure $P_1$ in the range of from 37 psia (255.1 kPa) to 100 psia (689.5 kPa), at a WHSV in the range of from 0.1 hr$^{-1}$ to 20 hr$^{-1}$, such as from 0.25 hr$^{-1}$ to 2 hr$^{-1}$. Typically, the first product comprises substantially the entire effluent of the first reactor, and typically substantially the entire first product is transferred to the second reactor. The first product reacts in the second reactor in the presence of Catalyst B while exposed to a temperature $T_2$ in the range of from 500° C. to 675° C. and a pressure $P_2 \leq 32$ psia (220.6 kPa), at a WHSV in the range of from 0.1 hr$^{-1}$ to 20 hr$^{-1}$, such as from 0.25 hr$^{-1}$ to 2 hr$^{-1}$, and typically less than the WHSV used when reacting the feed in the presence of catalyst A. More particularly, $T_1 \leq 0.9 \cdot T_2$ and $P_2 \leq 0.9 \cdot P_1$, with $P_2$ in the range of 1 psia to 32 psia (220.6 kPa), e.g., 5 psia (34.5 kPa) to 30 psia (206.8 kPa), or 5 psia (34.5 kPa) to 29 psia (199.9 kPa).

All patents, test procedures, and other documents cited herein, including priority documents, are fully incorporated by reference to the extent such disclosure is not inconsistent and for all jurisdictions in which such incorporation is permitted. Although certain aspects are described herein with particularity, other aspects will be apparent to and can be readily practiced by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains. When lower and upper limits are specified, ranges from any lower limit to any upper limit are expressly within the scope of the invention. The term "comprising" is synonymous with the term "including". When a composition, an element or a group of components is preceded with the transitional phrase "comprising", the same composition or group of components is within transitional phrases "consisting essentially of," "consisting of," "selected from the group of consisting of," or "is" preceding the recitation of the composition, component, or components, and vice versa.

The invention claimed is:

1. A hydrocarbon conversion process, comprising:
   (a) providing a feed comprising $\geq 1$ wt. % of $C_{2+}$ non-aromatic hydrocarbon and $\geq 0.1$ wt. % of $CO_2$;
   (b) providing first and second catalysts, wherein
      the first catalyst includes (i) $\geq 0.005$ wt. % of a dehydrogenation component which comprises one or more of Ga, Zn, Mo, W, La, Pt, and Pd, and (ii) $\geq 10$ wt. % of a molecular sieve component, the molecular sieve component comprising at least one molecular sieve having a Constraint Index in the range of from 1 to 12, and
      the second catalyst includes $\geq 0.005$ wt. % of a $CO_2$ conversion component which comprises one or more of Ru, Rh, Ni, Co, and Fe;
   (c) exposing the feed to the first catalyst under conversion conditions effective for (i) converting $\geq 10$ wt. % of the feed's $C_{2+}$ non-aromatic hydrocarbon to aromatic hydrocarbon and molecular hydrogen and (ii) increasing aromatic hydrocarbon yield by reacting $\geq 1$ wt. % of the feed's $CO_2$ with at least a portion of the molecular hydrogen in the presence of the second catalyst to produce methane and water.

2. The process of claim 1, wherein the feed comprises $\geq 1$ wt. % of $CO_2$; 10 wt. % to 40 wt. % ethane; 20 wt. % to 50 wt. % propane, and 20 wt. % to 50 wt. % butanes, and further comprises 1 wt. % to 40 wt. % methane and $\leq 1$ wt. % of aromatic hydrocarbon.

3. The process of claim 1, wherein the $CO_2$ reaction of step (c) has a greater selectivity for methane than CO.

4. The process of claim 1, wherein (i) the first catalyst includes (i) $\geq 0.01$ wt. % of the dehydrogenation component; (ii) the first catalyst's dehydrogenation component includes one or more of Ga, Zn, Mo, W, and La; and (iii) the first catalyst's molecular sieve component includes one or more of MCM-22, ZSM-5, ZSM-11, ZSM-12, ZSM-22, ZSM-23, ZSM-35, and ZSM-48.

5. The process of claim 1, wherein the second catalyst comprises $\geq 1$ wt. % of the $CO_2$ conversion component and further comprises $\geq 1$ wt. % of one or more of oxide of chromium, oxide of aluminum, oxide of magnesium, oxide of manganese, oxide of cerium, oxide of zirconium, oxide of titanium, and oxide of thorium.

6. The process of claim 1, wherein,
   (i) the first catalyst includes $\geq 50$ wt. % of the molecular sieve component and at least 1 wt. % of the first dehydrogenation component;
   (ii) the molecular sieve component comprises $\geq 90$ wt. % of (A) ZSM-5 and/or (B) ZSM-12;
   (iii) the first catalyst comprises $\geq 1$ wt. % of the dehydrogenation component;
   (iv) the dehydrogenation component comprises $\geq 90$ wt. % of (A) Ga and/or (B) Zn;
   (v) the second catalyst comprises $\geq 1$ wt. % of the $CO_2$ conversion component;
   (vi) the $CO_2$ conversion component comprises $\geq 90$ wt. % of one or more of Ru, Rh, and Ni; and
   (vii) the first and second catalysts are included in a catalyst composite, the catalyst composite comprising $\geq 10$ wt. % of the first catalyst and $\geq 10$ wt. % of the second catalyst.

7. The process of claim 1, wherein the conversion conditions include a temperature $T_1$ in range of from 400° C. to 700° C., a pressure $P_1 \geq 10$ psia (68.9 kPa), and a weight hourly space velocity (WHSV) in the range of 0.1 hr$^{-1}$ to 20 hr$^{-1}$.

8. The process of claim 7, further comprising:
   (d) recovering ethane from step (c), at least a portion of the recovered ethane being derived from unconverted feed and/or the conversion of step (c),
   (e) providing a third catalyst, wherein
      the third catalyst includes (i) $\geq 0.005$ wt. % of a dehydrogenation component, the dehydrogenation component being one or more of Ga, Zn, Mo, W, La, Pt, and Pd, and (ii) $\geq 10$ wt. % of a molecular sieve component comprising at least one molecular sieve having a Constraint Index in the range of from 1 to 12; and
   (f) converting $\geq 50$ wt. % of the recovered ethane in the presence of the third catalyst under conversion conditions including a temperature $T_2$ in the range of from 400° C. to 700° C., a pressure $P_2$ that is $\leq P_1$, and a WHSV in the range of 0.1 hr$^{-1}$ to 20 hr$^{-1}$.

9. The process of claim 8, wherein
   (i) $T_1$ is in the range of from 450° C. to 605° C. and $P_1$ is in the range of from 37 psia (255.1 kPa) to 80 psia (522 kPa);

(ii) $T_2$ is in the range of from 500° C. to 675° C. and $P_2 \leq 30$ psia (207 kPa);
(iii) no more than 50 wt. % of the feed's $CO_2$ is reacted in step (c); and wherein the process further comprises recovering unreacted feed $CO_2$ from step (c), and reacting ≥50 wt. % of the recovered $CO_2$ during step (f) in the presence of a fourth catalyst to increase aromatic hydrocarbon yield in step (f), the fourth catalyst comprising ≥0.005 wt. % of a $CO_2$ conversion component which includes one or more of Ru, Rh, Ni, Co, and Fe.

10. The process of claim 9, wherein
(i) the first catalyst's dehydrogenation component comprises ≥95 wt. % Ga, the first catalyst's dehydrogenation component being present in the first catalyst in an amount ≥0.1 wt. %;
(ii) the first catalyst's molecular sieve component comprises ≥90 wt. % of aluminosilicate having a silica:alumina ratio in the range of from 50 to 80;
(iii) the third catalyst's dehydrogenation component comprises ≥95 wt. % Zn, the third catalyst's dehydrogenation component being present in the third catalyst in an amount ≥0.1 wt. %; and
(iv) the third catalyst's molecular sieve component comprises ≥90 wt. % of aluminosilicate having a silica:alumina ratio in the range of from in the range of from 10 to 40.

* * * * *